＝

US009795545B2

(12) United States Patent
Fassih et al.

(10) Patent No.: US 9,795,545 B2
(45) Date of Patent: *Oct. 24, 2017

(54) COMPOSITIONS AND METHODS FOR ENHANCING THE TOPICAL APPLICATION OF A COLOR COSMETIC

(71) Applicant: JOHNSON & JOHNSON CONSUMER INC., Skillman, NJ (US)

(72) Inventors: Ali Fassih, Franklin Park, NJ (US); Anna Prilutsky, Princeton, NJ (US); Ying Sun, Belle Mead, NJ (US); Vivian Zhu, Flemington, NJ (US)

(73) Assignee: Johnson & Johnson Consumer Inc., Skillman, NJ (US)

(*) Notice: Subject to any disclaimer, the term of this patent is extended or adjusted under 35 U.S.C. 154(b) by 7 days.

This patent is subject to a terminal disclaimer.

(21) Appl. No.: 14/722,274

(22) Filed: May 27, 2015

(65) Prior Publication Data

US 2015/0359713 A1 Dec. 17, 2015

Related U.S. Application Data

(60) Provisional application No. 62/012,948, filed on Jun. 16, 2014.

(51) Int. Cl.
| | |
|---|---|
| *A61K 8/25* | (2006.01) |
| *A61K 8/11* | (2006.01) |
| *A61Q 1/00* | (2006.01) |
| *A61Q 1/02* | (2006.01) |
| *A61K 8/34* | (2006.01) |
| *A61K 8/73* | (2006.01) |
| *A61K 8/02* | (2006.01) |

(52) U.S. Cl.
CPC .............. *A61K 8/25* (2013.01); *A61K 8/0245* (2013.01); *A61K 8/11* (2013.01); *A61K 8/345* (2013.01); *A61K 8/732* (2013.01); *A61Q 1/00* (2013.01); *A61Q 1/02* (2013.01); *A61K 2800/56* (2013.01); *A61K 2800/652* (2013.01)

(58) Field of Classification Search
None
See application file for complete search history.

(56) References Cited

U.S. PATENT DOCUMENTS

| | | | |
|---|---|---|---|
| 3,393,155 | A | 7/1968 | Schutte et al. |
| 4,274,883 | A | 6/1981 | Lumbeck et al. |
| 5,229,076 | A | 7/1993 | Fagher |
| 6,174,533 | B1 | 1/2001 | SaNogueira, Jr. et al. |
| 6,290,941 | B1 | 9/2001 | Lahanas et al. |
| 6,419,913 | B1 | 7/2002 | Niemiec et al. |
| 6,534,647 | B1 | 3/2003 | Stevens et al. |
| 6,544,530 | B1* | 4/2003 | Friedman ............... A61K 8/06 424/400 |
| 6,946,120 | B2 | 9/2005 | Wai-Chiu So et al. |
| 7,417,020 | B2 | 8/2008 | Fevola et al. |
| 7,476,222 | B2 | 1/2009 | Sun et al. |
| 7,477,939 | B2 | 1/2009 | Sun et al. |
| 7,477,940 | B2 | 1/2009 | Sun et al. |
| 7,829,600 | B1 | 11/2010 | Trksak et al. |
| 8,163,311 | B2 | 4/2012 | Bruning et al. |
| 8,258,250 | B2 | 9/2012 | Fevola et al. |
| 8,475,689 | B2 | 7/2013 | Sun et al. |
| 8,647,653 | B2 | 2/2014 | Eng |
| 8,734,421 | B2 | 5/2014 | Sun et al. |
| 2002/0006418 | A1 | 1/2002 | Kung et al. |
| 2002/0012640 | A1* | 1/2002 | Mohammadi ............ A61K 8/19 424/59 |
| 2003/0017202 | A1 | 1/2003 | Bunick |
| 2003/0170191 | A1 | 9/2003 | Imamura |
| 2004/0067244 | A1 | 4/2004 | Friedman |
| 2005/0084510 | A1 | 4/2005 | Carson |
| 2005/0163811 | A1 | 7/2005 | Lee |
| 2005/0220860 | A1 | 10/2005 | Kim |
| 2005/0255134 | A1 | 11/2005 | Hasenzahl et al. |
| 2006/0008485 | A1 | 1/2006 | Ferone et al. |
| 2007/0154426 | A1 | 7/2007 | Hansen et al. |
| 2008/0038302 | A1 | 2/2008 | Tanaka |
| 2008/0095724 | A1 | 4/2008 | Hasenzahl et al. |
| 2009/0047225 | A1 | 2/2009 | Hasenzahl et al. |
| 2010/0203096 | A1 | 8/2010 | Tanaka et al. |
| 2010/0266647 | A1 | 10/2010 | Dingley et al. |
| 2010/0268335 | A1 | 10/2010 | Yang et al. |
| 2011/0082105 | A1 | 4/2011 | Fevola et al. |
| 2011/0082290 | A1 | 4/2011 | Gardner et al. |
| 2011/0104091 | A1 | 5/2011 | Maitra et al. |

(Continued)

FOREIGN PATENT DOCUMENTS

| | | |
|---|---|---|
| EP | 1235554 | 10/2000 |
| EP | 1206928 A | 5/2002 |

(Continued)

OTHER PUBLICATIONS

U.S. Appl. No. 13/719,649, Fassih et al.
Anonymous: "Moisturizing Hair Styling Powder", Feb. 1, 2013, pp. 1-2.
Anonymous: "Glycerin", Jun. 10, 2015, pp. 1-2.
Bjorklund Sebastian et al., "Glycerol and urea can be used to increase skin permeability in reduced hydration conditions", European Journal of Pharmaceutical Sciences, vol. 50, No. 5, May 3, 2013, pp. 638-645.
Bhosale, P.S., "Mechanically Robust Nanoparticle Stabilized Transparent Liquid Marbles", Applied Physics Letters 93, 034109 (2008).
Carrier, O., et al., "Inverse emulsions stabilized by a hydrophobically modified polysaccharide", Carbohydrate Polymers, 84 (2011), pp. 599-604.

(Continued)

*Primary Examiner* — Johann R Richter
*Assistant Examiner* — Katherine Peebles

(57) ABSTRACT

A powder is disclosed including a first powder of core/shell particles having an average particle size of less than 1000 microns, each particle contains a liquid core that is substantially free of water that includes a polar liquid having a percent surface polarity of at least 24%; and a shell comprising hydrophobic particles and a second powder including a color cosmetic.

8 Claims, No Drawings

(56) References Cited

U.S. PATENT DOCUMENTS

| | | |
|---|---|---|
| 2011/0135583 A1 | 6/2011 | Breffa et al. |
| 2011/0195100 A1 | 8/2011 | Bruning et al. |
| 2012/0021014 A1 | 1/2012 | Chantalat et al. |
| 2012/0315312 A1 | 12/2012 | Riedemann et al. |
| 2013/0022656 A1* | 1/2013 | Eng .................. A61K 8/0237 424/401 |
| 2014/0302106 A1 | 10/2014 | Knappe et al. |

FOREIGN PATENT DOCUMENTS

| | | |
|---|---|---|
| EP | 1386599 | 2/2004 |
| JP | 2000-309505 | 11/2000 |
| WO | WO 01/85138 | 11/2001 |
| WO | WO 2011/075418 | 6/2011 |
| WO | WO 2011/076518 | 6/2011 |
| WO | 2013/087311 A2 | 6/2013 |
| WO | WO 2014/099946 | 6/2014 |

OTHER PUBLICATIONS

Claro, C., et al., "Surface tension and rheology of aqueous dispersed systems containing a new hydrophobically modified polymer and surfactants", International Journal of Pharmaceutics, 347 (2008), pp. 45-53.

Chedea, V.S. et al., "Composition in Polyphenols and Stability of the Awueous Grape Seed Extract from the Romanian Variety Merlot Recas", J. Food Biochem, 35 (2011) pp. 92-108.

Drelich et al., "Measurement of Interfacial Tension in Fluid-Fluid Systems", Encyclopedia of Surface and Colloid Science, (2002), pp. 3152-3166.

Eshtiaghi et al., Powder Technology, vol. 223, (2012), pp. 65-76.

Forny, L. et al., "Influence of mixing characteristics for water encapsulation by self-assembling hydrophobic silica nanoparticles," Powder Technology 189, (2009), pp. 263-269.

Fowkes, F.M., Journal of Physical Chemistry, 67 (1963), pp. 2538-2541.

Lochhead et al., "Polymers in Cosmetics: Recent Advances", Article Jul. 2004, Happi.com.

Tadros, T., "Polymeric Surfactants in Disperse Systems", Advances in Colloid and Interface Science 147-148, (2009) pp. 281-299.

Takahashi et al., "Proanthocyanidins from Grape Seeds Promote Proliferation of Mouse Hair Follicle Cells In vitro and Convert Hair Cycle In vivo", Acta Derm Venereol, 78 (1998) pp. 428-432.

Takahashi et al., "Procyanidin Oligomers Selectively and Intensively Promote Proliferation of Mouse Hair Epithelial Cells In Vitro and Activate Hair Follicle Growth In Vivo", J. Invest. Derm., 112:3 (1999) pp. 310-316.

Takahashi et al., "Procyanidin B-3, isolated from barley and identified as a hair-growth stimulant, has the potential to counteract inhibitory regulation by TGF-β1", Exp. Derm., 11 (2002) pp. 532-541.

Zenkiewicz, M., "Methods for the calculation of surface free energy of solids", Journal of Achievements in Materials and Manufacturing Engineering, 24, 1, (2007) 137-145.

International Search Report for PCT/US2013/075714 dated Apr. 24, 2014.

International Search Report for PCT/2015/019588 dated Jun. 24, 2015.

International Search Report for PCT/2015/019589 dated Jun. 24, 2015.

International Search Report dated Aug. 10, 2015 for Application No. PCT/US2015/033461.

Boonton, et al., "Polymeric, Carbohydrate-Based Surfactants and their Use in Personal Care Applications", SOFW-Journal 130(8):10-16, 2004: http://creachem.be/Portals/O/Cosm%20App/SOFW_2004_UK.pdf.

Beneo's Practical Guidelines to INUTEC SP1, dated Dec. 28, 2009: http://protective.com/au/pdfs/Guidelines-Inutec-SP1-0912-2010.pdf.

Lemmens et al., "Preparation and stabilization of transparent nano-emulsions using inulin-based surfactants", Research Disclosure 499:1355-1356 (2005).

* cited by examiner

COMPOSITIONS AND METHODS FOR ENHANCING THE TOPICAL APPLICATION OF A COLOR COSMETIC

CROSS REFERENCE TO RELATED APPLICATIONS

This application claims priority of the benefits of U.S. Provisional Application Ser. No. 62/012,948 filed Jun. 16, 2014. The complete disclosure of the aforementioned related U.S. patent application is hereby incorporated by reference for all purposes.

The present invention relates to compositions and methods for enhancing the topical application of a color cosmetic. The compositions are a first powder of powder-to-liquid particles comprising a liquid core that is substantially free of water that comprises a polar liquid that has a percent surface polarity of at least 24% surrounded by a shell comprising hydrophobic particles and a second powder including a color cosmetic. The particles are stable in dry form and yet quickly transform into a liquid or cream-like form when subjected to shear. They can be advantageously formulated with other ingredients into personal care compositions.

BACKGROUND OF THE INVENTION

It is known that in the presence of a hydrophobic powder, such as a hydrophobic silicon dioxide powder (silicone-coated silica powder), water can be dispersed into fine droplets and enveloped by the hydrophobic material, thus preventing the droplets from rejoining. Such material has been described as "dry water," "powdered water," or "powder-to-liquid" and can have a water content of over 95%. It is formed by the intensive mixing of water with hydrophobic material. During this process water droplets are sheathed by the solid particles and prevented from flowing together again. The first experiments on the use of "dry water" as a cosmetic base date from the 1960's. See U.S. Pat. No. 3,393,155. These free-flowing, fine powders liquefy when rubbed on the skin.

More recently, U.S. Pat. No. 6,290,941 describes cosmetic or pharmaceutical powder-to-liquid compositions comprising hydrophobically coated silica particles into which are incorporated water and a water soluble polymer, the composition containing substantially no oil. Such compositions are said to require less silica while retaining the water-holding capacity and permitting substantial elimination of added oil from the formula. The particles can be used with color cosmetics.

WO 2011/075418 discloses a powdery composition comprising a) at least one powder in the form of core-shell particles, the core comprising liquid water or a liquid aqueous phase and the shell comprising hydrophobic or hydrophobized particles, and b) at least one powder comprising carrier, and b1) at least partially water soluble liquid and/or b2) a water reactive substrate each located in and/or on the carrier.

Eshtiaghi et al., *Powder Technology*, Vol. 223, 2012, pages 65-76 describes a variety of powder-to-liquid materials and proposes mechanisms for their formation. Shell materials used included hydrophobic (silicone-coated) silica, hydrophobic glass beads and polytetrafluoroethylene (PTFE or TEFLON) powder. Core materials included water, glycerol, and polyethylene glycol (PEG). Reported particle sizes for materials containing glycerin were 1200 and 3400 microns.

US 2012/0315312 teaches core-shell particles, the shell of which includes aggregated, hydrophobicized silicon dioxide particles and the core of which includes a liquid phase. The ratio of the silicon dioxide particles to the liquid phase is 2:98 to 40:60 based on the total weight of the particles and 60-100% by weight of glycerol is present in the liquid phase.

U.S. application Ser. No. 13/719,649, filed Dec. 19, 2012 teaches a powder comprising core/shell particles having an average particle size of less than 1000 microns, each particle comprising: 1) a liquid core that is substantially free of water and comprises a polar liquid having a percent surface polarity of at least 24%, and 2) a shell comprising hydrophobic particles. The particles can include an active.

Color cosmetics, such as eye shadow, foundation, blush, concealer and the like are commercially available in powder form. They are used to enhance facial appearance and cover up imperfections. The powder includes inorganic and/or organic pigments. The powder may be applied by brush or pad. It is highly desirable to have skin color cosmetic products not only provide make-up effects (e.g., cover/mask skin infection by colored powder and pigments), but also deliver true benefits to the skin, e.g., moisturization (to prevent facial skin from being flakey and itchy), and removal of excess sebum oil (to prevent blockage of hair follicles or the opening of the sebaceous ducts to cause acne or blackheads). However, it is difficult to provide the benefits of both moisturization and sebum removal from the same color cosmetic product (e.g., a facial foundation powder), since most skin moisturizing agents are oily substances and tend to block skin pores. Over-removing sebum leads to symptoms of dry skin. There is a need for improved color cosmetic compositions.

Applicants have now discovered novel compositions and a method of enhancing the topical application of color cosmetics. The compositions include powder-to-cream particles containing a liquid core and a powder shell. Compositions containing such particles are also convenient to use while providing a cream-like, pleasant skin feel and skin substantivity (the ability to remain on the skin). The compositions can be used in cosmetic, skin care, and other personal care products, as well as in other applications and industries.

SUMMARY OF THE INVENTION

The invention provides a powder including a powder of core/shell particles having an average particle size of less than 1000 microns, each particle contains a liquid core that is substantially free of water that includes a polar liquid having a percent surface polarity of at least 24%; and a shell comprising hydrophobic particles and a second powder including a color cosmetic.

Incorporation of the core/shell particles of the present invention into a conventional cosmetic product, for example, a foundation powder, yields a novel foundation powder with both cosmetic as well as physiologically important skin benefits. The invention also provides a method for topically administering the active ingredient by rubbing the powder on the skin of a human or animal.

DETAILED DESCRIPTION OF THE INVENTION

As used herein, unless otherwise specified, all percentages are by weight based on the total weight of composition referred to.

The disclosures of all patents and published applications referred to herein are incorporated by reference in their entirety.

As used herein, "substantially free" of an ingredient means containing about 5% by weight or less of that ingredient. Preferably, substantially free of an ingredient means containing about 2% or less, or about 1% or less, or about 0.5% or less or about 0.1% or less, or about 0.05% or less, or about 0.01% or less, by weight of such ingredient. In certain embodiments, substantially free of an ingredient means completely free of the ingredient, i.e., containing none of that ingredient.

As used herein, an "active agent" or "benefit agent" is a compound (e.g., a synthetic compound or a compound isolated from a natural source) that has a cosmetic or therapeutic effect on tissue (e.g., a material capable of exerting a biological effect on the human body) such as therapeutic drugs or cosmetic agents. Examples of active agents include small molecules, peptides, proteins, nucleic acid materials, and nutrients such as minerals and plant extracts. The amount of the active agent used will depend on the active agent and/or the intended use of the end product. Active agents or benefit agents may be liquid, solid, or semi-solid. Further, active agents or benefit agents may be incorporated into the liquid core and/or the shell of the core/shell particles.

As used herein, "pharmaceutically acceptable," "cosmetically acceptable," or "dermatologically acceptable" means suitable for use in contact with tissues (e.g., the skin, hair, mucosa, epithelium or the like) without undue toxicity, incompatibility, instability, irritation, or allergic response.

As used herein, "safe and effective amount" means an amount sufficient to provide a desired benefit at a desired level, but low enough to avoid serious side effects. The safe and effective amount of the ingredient or composition will vary with the area being treated, the age of the end user, the duration and nature of the treatment, the specific ingredient or composition employed, the particular carrier utilized, and like factors.

As used herein, the term "treating" or "treatment" means the alleviation or elimination of symptoms, cure, prevention, or inhibition of a disease or medical condition, or improvement of tissue growth/healing or cosmetic conditions such as reducing appearance of skin wrinkles/fine lines, under-eye bags, cellulites, skin marks/hyperpigmentation or uneven tone.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

To provide a more concise description, some of the quantitative expressions herein are recited as a range from about amount X to about amount Y. It is understood that wherein a range is recited, the range is not limited to the recited upper and lower bounds, but rather includes the full range from about amount X through about amount Y, or any amount or range therein.

Core/Shell Particles

The first powder of the invention comprises core/shell particles. Each particle comprises a liquid core that comprises a polar liquid. The polar liquid has a minimum surface polarity. The liquid core is surrounded by a shell of hydrophobic particles and a color cosmetic.

Particles according to the present invention have a liquid core surrounded by a shell of hydrophobic particles. The liquid core that is substantially free of water includes an emulsion or suspension comprising a polar liquid as the continuous (external) phase. The dispersed (internal) phase comprises a hydrophobic material and/or solid particles.

The hydrophobic particles of the shell are in the form of loose powder held together only by weak liquid-powder and powder-powder interactions via weak van der Waals forces. When subjected to slight forces such as by rubbing with the hands, the core/shell particles collapse and the powder becomes a liquid, cream or gel.

Overall, the average particle size of the core/shell particles is less than about 1000 micrometers, usually from about 1 micrometer to about 1000 micrometers, or about 2 micrometers to about 200 micrometers, or about 3 micrometers to about 100 micrometers, or about 5 micrometers to about 50 micrometers. The average particle size of the core/shell particles can be determined by any particle size measurement method for dry particles known to the art, such as optical microscopy, electron microscopy, or sieve analysis.

The Core

The liquid core comprises a polar liquid that has a minimum polar component of overall surface tension. As known in the art, the surface tension of a liquid (i.e., overall surface tension) is divided into two components, one representing a polar component and one representing a nonpolar (or dispersive) component. The polar component, "percent (%) surface polarity," is determined using the method of Fowkes described in Fowkes, *Journal of Achievements in Materials and Manufacturing Engineering*, 24, 1 (2007) 137-145.

Specifically, the overall surface tension of a sample is measured five times via the Wilhelmy plate method (described by Derelinch et. al. "Measurement of Interfacial Tension in Fluid-Fluid Systems", in *Encyclopedia of Surface and Colloid Science*, pages 3152-3166, Ed. By Arthur T. Hubbard, Marcel Dekker, Inc., 2002), using a Kruss Tensiometer K100. The plate used is a standard platinum plate of 19.9 mm×0.2 mm perimeter.

The contact angle of each sample is also measured five times on a clean piece of poly(tertafluoroethylene) PTFE using a Kruss Drop Shape Analysis System DSA10. Measuring contact angle on PTFE is done as a means of separating the overall surface tension of each sample into polar and dispersive components. According to the Fowkes surface energy theory, the dispersive component of a liquid can be determined by knowing its overall surface tension and its contact angle against PTFE (which is a completely non-polar surface). The equation is as follows:

$$\sigma_L^D = \frac{\sigma_L^2(\cos\theta_{PTFE} + 1)^2}{72}$$

where $\theta_{PTFE}$=the contact angle measured between PTFE and the sample liquid. The dispersive surface tension component ($\sigma_L^D$) can be determined for any liquid for which the overall surface tension ($\sigma_L$) is known simply by measuring the contact angle between that liquid and PTFE ($\theta_{PTFE}$) and using the equation above. The polar surface tension component for the liquid is then determined by difference ($\sigma_L^P = \sigma_L - \sigma_L^D$). The percent surface polarity is ($\% = \sigma_L^P * 100\%/\sigma_L$). See also F. M. Fowkes, *Journal of Physical Chemistry*, 67 (1963) 2538-2541.

The polar liquid has a percent surface polarity of at least 24%, or at least 25%, or at least 26%, or at least 30%.

The liquid core may be a single phase (one-phase). Alternatively, the liquid core may comprise multiple phases, for example the liquid core may be an emulsion or a suspension.

In one embodiment, the liquid core is a substantially, or completely uniform single phase, namely, it is a homogeneous clear liquid containing no visibly detectable inhomogeneities, such as suspended droplets or particles when viewed with the unaided human eye at a distance of approximately 12 inches. The liquid core as a single phase may contain other organic liquids besides the polar liquid, so long as such organic solvents are soluble or substantially soluble, miscible or substantially miscible in the polar liquid to maintain the homogeneity and clarity of the liquid core. When other organic liquids that are partially soluble in or partially miscible with the polar liquid are used, their amounts should be below their saturation concentrations to ensure the liquid core remains a clear solution.

The polar liquid may comprise one or more polyols. Such polyols include, but are not limited to glycerol (glycerin), polyglycerols, glycols, polyglycols, and mixtures thereof.

Examples of polyglycerols include, but are not limited to diglycerol (diglycerin), triglycerol (polyglcerin-3 or polyglycerol-3), tetraglycerol (polyglycerin-4 or polyglycerol-4), other polyglycerols (polycerol-n, where n>4), and mixtures thereof.

Examples of glycols include, but are not limited to propylene glycol, ethylene glycol, butylene glycol and its isomers (e.g., 1,2-butanediol, 1,3-butanediol, 1,4-butanediol and 2,3-butanediol), hexylene glycol and its isomers, propanediol, dipropylene glycol, ethoxydiglycol, methylpropanediol, isopentyldiol, and mixtures thereof.

Examples of polyglycols include, but are not limited to, polyethylene glycol of various molecular weights, namely, molecular weights ranging from 300 g/mol to 10,000,000 g/mol, (e.g., PEG-200, PEG-400, PEG-1000, PEG-2000 PEG-4000, PEG-6000), polypropylene glycol (PPG) of various molecular weights, and mixtures thereof.

The polar liquid may comprise a combination of a polyol with one or more other organic liquids. Such organic liquids include, but are not limited to alcohols, isosorbides, esters, ethers, lactones, and any organic compounds acceptable for therapeutic, cosmetic or personal product applications and capable of maintaining the percent surface polarity of the polar liquid at 24% or above.

Examples of alcohols include, but are not limited to ethyl alcohol, n-propyl alcohol, isopropyl alcohol, n-butyl alcohol, isobutyl alcohol, amyl alcohol, benzyl alcohol, octyldocanol, hexyldecanol, butyloctanol, and mixtures thereof.

Examples of isosorbides include, but are not limited to dimethyl isosorbide, diethyl isosorbide, ethylmethyl isosorbide, and mixtures thereof. Preferably, the isosorbide is an alkyl ester of isosorbide, such as dimethyl isosorbide.

Examples of esters include, but are not limited to benzyl benzoate, triacetin, glycerol trioctanoate, diethyl phthalate, and mixtures thereof.

Examples of ethers include, but are not limited to dicapryl ether, dipropylene glycol monomethyl ether, and mixtures thereof.

Examples of lactones include but are not limited to gluconolactone.

In one embodiment of the invention, the polar liquid is a mixture of a glycerol or polyglycerol with one or more glycols or polyglycols.

In an alternative embodiment of the invention, the polar liquid is a mixture of a glycerol or polyglycerol with one or more alcohols.

In yet another embodiment of the invention, the polar liquid is a mixture of a glycerol or polyglycerol with one or more isosorbides.

Preferably, the polar liquid comprises a glycerol, polyglycerol, or a mixture thereof. The amount of glycerol, polyglycerol, or mixture thereof may be about 50% to about 100%, or more than about 70%, or more than about 80%, or 85% or more, by weight of the polar liquid of the liquid core. The remainder of the liquid core may be one or more organic liquids such as non-glycerol polyols, alcohols, or isosorbides.

In one embodiment, the liquid core may further comprise at least one hydrophilic polymer, e.g., natural or synthetic hydrophilic polymers. Such hydrophilic polymer may be soluble or partially soluble in the liquid core. Suitable hydrophilic polymers include, but are not limited to, homo- and copolymers of vinyl pyrrolidone (e.g., PVP, or PVP/PVA copolymer), homo-or copolymers of vinyl alcohol (e.g., polyvinyl alcohol or PVA), polyacrylamide, homo-or copolymers of acrylic and/or methacrylic acids, and salts and esters thereof (e.g., CARBOPO/CARBOMER 934, 940, 941, 980, 1342, and 1382, and ULTREZ 10 and 21), cellulosic polymers (e.g., hydroxymethylcellulose, hydroxyethyl cellulose, carboxy methyl cellulose, carboxy ethyl cellulose), polyurethanes, starch and its derivatives, and synthetic and natural gums (e.g., gum arabic or xanthan gum). Preferred hydrophilic polymers are acrylate polymers and copolymers, particularly polyacrylate neutralized by anhydrous neutralizers.

Incorporation of such polymers in the liquid core enhances interactions between the liquid core and the hydrophobic particles of the shell, thereby facilitating core-shell particle formation and improving the physical stability of the core/shell particles, which prevents premature particle collapse and liquid leakage during storage.

If used, the amount of the hydrophilic polymer is usually up to about 10%, or equal to or less than about 5%, or equal to or less than about 3%, or equal to or less than about 2%, by weight of the liquid core.

In a further embodiment the liquid core may further include silicone or silicone oil. The core may be an oil in glycerol emulsion or a silicone oil in glycerol emulsion.

In general, the liquid core may contain any additional ingredients (e.g., active agents or formulation excipients) soluble or dispersible in the polar liquid or its components, provided the additional ingredients do not impair the percent surface polarity of the liquid core. Pharmaceutically or cosmetically acceptable active agents or excipients, such as extracts of plants or minerals, natural or synthetic compounds of small molecular weight or polymers, acids or bases (particularly week acids or bases) for acidity adjustment, buffers, chelators, antioxidants, thickeners or gelling agents can be used.

In particular, the active agents or benefit agents are present in the liquid core. The liquid core may also comprise one or more emulsifying surfactants (emulsifiers) commonly used in pharmaceutical or cosmetic products.

In one embodiment, the liquid core comprises an emulsion (e.g., simple emulsion, multi-emulsion, or nano-emulsion), in which there is at least one internal phase (e.g., oil phase), and at least one external polar liquid phase (e.g., glycerol, polyglycerol, or other polyol phase) as the continuous phase of the liquid core. The internal phase includes at least one lipophilic substance, which is a liquid at ambient temperature, and is essentially immiscible with the external polar liquid phases. Non-limiting exemplary oils include oils of plant origins (e.g., vegetable oils and oil extracts of plants—seeds, legumes or fruits), mineral oils, silicone oils/fluids and their derivatives, and any lipophilic solvents acceptable for pharmaceutical, topical or cosmetic products.

The oils used for the internal oil phase of the liquid core may be volatile or nonvolatile in nature. Hydrophobic solvents suitable for use in the volatile, hydrophobic solvent component are selected from the group consisting of branched chain hydrocarbons, silicones, fatty acid esters, liquid branched chain fatty alcohols, and triglycerides (e.g., caprylic/capric triglyceride), isopropyl myristate, isopropyl palmitate, and mixtures, thereof. Preferred hydrophobic branched chain hydrocarbons useful as the solvent component herein contain from about 7 to about 14, more preferably from about 10 to about 13, and most preferably from about 11 to about 12 carbon atoms. Saturated hydrocarbons are preferred, although it is not intended to exclude unsaturated hydrocarbons. Examples of such preferred branched chain hydrocarbons include isoparaffins of the above chain sizes. Isoparaffins are commercially available form Exxon Chemical Co; examples include Isopar E ($C_8$-$C_9$ isoparaffins), Isopar™ H and K ($C_{11}$-$C_{12}$ isoparaffins), and Isopar™ L ($C_{11}$-$C_{13}$ isoparaffins) or mixtures thereof. Other suitable branched chain hydrocarbons are isododecane and isoundecane. Isododecane is preferred and is commercially available from Presperse, Inc. (South Plainfield, N.J., USA) as Permethyl™ M 99A.

Preferred silicones useful as the volatile hydrophobic solvent component include volatile siloxanes such as phenyl pentamethyl disiloxane, phenylethylpentamethyl disiloxane, hexamethyl disiloxane, methoxy propylheptamethyl cyclotetrasiloxane, chloropropyl pentamethyl disiloxane, hydroxypropyl pentamethyl disiloxane, octamethyl cyclotetrasiloxane, decamethyl cyclopentasiloxane, and mixtures thereof. More preferred among the silicones are cyclomethicones, examples of which include hexamethyl disiloxane, octamethyl cyclo tetrasiloxane and decamethyl cyclopentasiloxane, which are commonly referred to D4 and D5 cyclomethicone, respectively.

The internal phase of the oil(s) in the emulsion liquid core is physically stabilized by the surfactants in the emulsion liquid core. In one embodiment, the liquid core comprises at least one polymeric surfactant having a molecular weight ranging from about 1,000 Daltons to 50,000 Daltons, including, but not limited to, homo-polymers such as poly(ethylene oxide), poly(vinyl pyrrolidone) and poly(vinyl alcohol), block and graft copolymer polymeric surfactants such as diblock or triblock polymeric surfactants known as PLURONICS manufactured by BASF (Germany) or SYNPERONIC PE manufactured by ICI (U.K.) consisting of two poly-A blocks of poly(ethylene oxide)(PEO) and one block of poly(propylene oxide)(PPO), and diblocks of polystyrene-block-polyvinyl alcohol, triblocks of poly(methyl methacrylate)-block poly(ethylene oxide)-block poly (methyl methacrylate), diblocks of polystyrene block-polyethylene oxide and triblocks of polyethylene oxide-block polystyrene-polyethylene oxide, as well as amphipathic graft copolymer consisting of a polymeric backbone B (polystyrene or polymethyl methacrylate) and several A chains ("teeth") such as polyethylene oxide referred to as a "comb" stabilizer may be used.

In one embodiment, the liquid core comprises at least one hydrophobically modified polysaccharide. Useful polysaccharides include sugars (e.g., inulin), sugar analogs (e.g., dextrans), starches (e.g., starches from potato or tapioca), water-soluble celluloses (e.g., hydroxypropylcellulose), hydrophobically modified inulin (polyfructose) as disclosed in U.S. Pat. No. 6,534,647 (including commercially available INUTEC SP1 (ORAFTI, Tienen, Belgium), hydrophobically modified dextran as disclosed by O. Carrier et al. ("Inverse emulsions stabilized by a hydrophobically modified polysaccharide", Carbohydrate Polymers, 84(2011)599-604), hydrohobically modified starches from potato or tapioca as disclosed in U.S. Pat. Nos. 8,258,250, 7,417,020, US20110082105A1, and US 20110082290A1, (including commercially available NATURASURFTM PS-111, AKZO NOBEL CHEICALS INTERNATIONAL, B.V.), and hydrophobically modified water-soluble hydroxypropylcellulose as disclosed by C. Claro et al. ("Surface tension and rheology of aqueous dispersed systems containing a new hydrophobically modified polymer and surfactants", International Journal of Pharmaceutics, 347(2008)45-53). Other exemplary hydrophobically modified polysaccharides, include, but are not limited to, PEMULEN TR-1, PEMULEN TR-2, ETD 2020, CARBOPOL 1382 (Acrylates/C10-30 alkyl acrylate crosspolymer, by Noveon/Lubrizol, Cleveland, Ohio), NATROSOL CS Plus 330, 430, POLYSURF 67 (cetyl hydroxyethyl cellulose, Hercules, Wilmington, Del.), ACULYN 22 (acrylates /steareth-20 methacrylate copolymer, Rohm & Haas, Philadelphia, Pa.), ACULYN 25 (acrylates/laureth-25 methacrylate Copolymer, Rohm & Haas), ACULYN 28 (acrylates/beheneth-25 methacrylate copolymer, Rohm & Haas), ACULYN 46 (PRG-150/stearyl alcohol/SMDI copolymer, Rohm & Haas), STABYLEN 30 (acrylates/vinyl isodecanoate, 3V-Sigma, Georgetown, S.C.), STRUCTURE 2001 (acrylates/steareth-20 itaconate copolymer, National Starch), STRUCTURE 3001 (acrylates/ceteth-20 itaconate copolymer, National Starch), STRUCTURE PLUS (acrylates/aminoacrylates/C10-30 alkyl PEG 20 itaconate copolymer, National Starch), QUATRISOFT LM-200 (polyquaternium-24, Amerchol, Greensburg, La.), CAPSULE, HI-CAP 100, N-CREAMER 46, CAPSUL TA, and N-LOK-1930 (all by Ingredion Incorporated, formally National Starch or Corn Products International, Inc.), Westchester, Ill.

The amount of hydrophobically modified polysaccharide surfactant used is generally from about 0.01% to about 20%, or from about 0.1% to about 10%, or from about 0.5% to about 5%, or from about 0.1% to about 1%, by weight of the liquid core.

Other useful surfactants are described by T. Tadros ("Polymeric Surfactants in Disperse Systems", Advances in Colloid and Interface Science, 147-148,2009, page 281-299), and R.Y. Lochhead and S. Jones ("Polymers in Cosmetics: Recent Advances", Article 2004/07, Happi.com).

In one embodiment, the composition comprises at least one surfactant typically used to prepare oil-in-water (O/W) emulsions as disclosed in U.S. Pat. No. 6,174,533.

The liquid core may comprise from about 0.05% to about 5%, or from about 0.05% to about 1%, by weight of such surfactant. Without intending to be limited by theory, it is believed that the surfactant assists in dispersing the hydrophobic component in the polar liquid. The surfactant, at a minimum, must be hydrophilic enough to disperse in the hydrophilic component. Preferred surfactants are those having an HLB of at least about 8. The exact surfactant chosen will depend upon the pH of the composition and the other components present.

The surfactant can be any of the anionic surfactants, nonionic surfactants, amphoteric surfactants, zwitterionic surfactants cationic surfactants and mixtures clearly as are well known in the art.

Examples of nonionic surfactants that are useful herein are those that can be broadly defined as condensation products of long chain alcohols, e.g. C8-30 alcohols, with sugar or starch polymers, i.e., glycosides. These compounds can be represented by the formula $(S)_n$—O—R wherein S is a sugar moiety such as glucose, fructose, mannose, and galactose; n is an integer of from about 1 to about 1000, and R is a C8-30 alkyl group. Examples of long chain alcohols from which the alkyl group can be derived include decyl alcohol, cetyl alcohol, stearyl alcohol, lauryl alcohol, myristyl alcohol, oleyl alcohol, and the like. Examples of these surfactants include those wherein S is a glucose moiety, R is a C8-20 alkyl group, and n is an integer of from about 1 to about 9. Commercially available examples of these surfactants include decyl polyglucoside (available as APG 325 CS from Henkel) and lauryl polyglucoside (available as APG 600 CS and 625 CS from Henkel).

Other useful nonionic surfactants include the condensation products of alkylene oxides with fatty acids (i.e. alkylene oxide esters of fatty acids). These materials have the general formula $RCO(X)_nOH$ wherein R is a C10-30 alkyl group, X is —$OCH_2CH_2$— (i.e. derived from ethylene glycol or oxide) or —$OCH_2CHCH_3$— (i.e. derived from propylene glycol or oxide), and n is an integer from about 6 to about 200. Other nonionic surfactants are the condensation products of alkylene oxides with 2 moles of fatty acids (i.e. alkylene oxide diesters of fatty acids). These materials have the general formula $RCO(X)_nOOCR$ wherein R is a C10-30 alkyl group, X is —$OCH_2CH_2$— (i.e., derived from ethylene glycol or oxide) or —$OCH_2CHCH_3$— (i.e. derived from propylene glycol or oxide), and n is an integer from about 6 to about 100.

Other nonionic surfactants are the condensation products of alkylene oxides with fatty alcohols (i.e. alkylene oxide ethers of fatty alcohols). These materials have the general formula $R(X)_nOR'$ wherein R is a C10-30 alkyl group, X is —$OCH_2CH_2$— (i.e. derived from ethylene glycol or oxide) or —$OCH_2CHCH_3$— (i.e. derived from propylene glycol or oxide), and n is an integer from about 6 to about 100 and R' is H or a C10-30 alkyl group. Still other nonionic surfactants are the condensation products of alkylene oxides with both fatty acids and fatty alcohols (i.e. wherein the polyalkylene oxide portion is esterified on one end with a fatty acid and etherified (i.e. connected via an ether linkage) on the other end with a fatty alcohol). These materials have the general formula $RCO(X)_nOR'$ wherein R and R' are C10-30 alkyl groups, X is —$OCH_2CH_2$ (i.e., derived from ethylene glycol or oxide) or —$OCH_2CHCH_3$ — (derived from propylene glycol or oxide), and n is an integer from about 6 to about 100. Nonlimiting examples of these alkylene oxide derived nonionic surfactants include ceteth-6, ceteth-10, ceteth-12, ceteareth-6, ceteareth-10, ceteareth-12, steareth-6, steareth-10, steareth-12, PEG-6 stearate, PEG-10 stearate, PEG-100 stearate, PEG-12 stearate, PEG-20 glyceryl stearate, PEG-80 glyceryl tallowate, PEG-10 glyceryl stearate, PEG-30 glyceryl cocoate, PEG-80 glyceryl cocoate, PEG-200 glyceryl tallowate, PEG-8 dilaurate, PEG-10 distearate, and mixtures thereof.

Other nonionic surfactants suitable for use herein include sugar esters and polyesters, alkoxylated sugar esters and polyesters, C1-C30 fatty acid esters of C1-C30 fatty alcohols, alkoxylated derivatives of C1-C30 fatty acid esters of C1-C30 fatty alcohols, alkoxylated ethers of C1-C30 fatty alcohols, polyglyceryl esters of C1-C30 fatty acids, C1-C30 esters of polyols, C1-C30 ethers of polyols, alkyl phosphates, polyoxyalkylene fatty ether phosphates, fatty acid amides, acyl lactylates, and mixtures thereof. Nonlimiting examples of these non-silicon-containing emulsifiers include: polyethylene glycol 20 sorbitan monolaurate (Polysorbate 20 or TWEEN 20), polyethylene glycol 5 soya sterol, Steareth-20, Ceteareth-20, PPG-2 methyl glucose ether distearate, Ceteth-10, Polysorbate 80 (TWEEN 80), Polysorbate 40 (TWEEN 40), cetyl phosphate, potassium cetyl phosphate, diethanolamine cetyl phosphate, Polysorbate 60 (TWEEN 60), glyceryl stearate, polyoxyethylene 20 sorbitan trioleate (Polysorbate 85), sorbitan monolaurate, polyoxyethylene 4 lauryl ether sodium stearate, polyglyceryl-4 isostearate, hexyl laurate, PPG-2 methyl glucose ether distearate, PEG-100 stearate, and mixtures thereof.

Other emulsifiers useful herein are fatty acid ester blends based on a mixture of sorbitan or sorbitol fatty acid ester and sucrose fatty acid ester, the fatty acid in each instance being preferably C8-C24, more preferably C-10-C20. The preferred fatty acid ester emulsifier is a blend of sorbitan or sorbitol C 16-C20 fatty acid ester with sucrose C10-C16 fatty acid ester, especially sorbitan stearate and sucrose cocoate. This is commercially available from ICI under the trade name ARLATONE 2121.

The surfactants useful herein can alternatively or additionally include any of a wide variety of cationic, anionic, zwitterionic, and amphoteric surfactants such as are known in the art. Cationic surfactants useful herein include cationic ammonium salts such as quaternary ammonium salts, and amino-amides. Nonlimiting examples of anionic surfactants include the alkoyl isethionates (e.g., C12-C30), alkyl and alkyl ether sulfates and salts thereof, alkyl and alkyl ether phosphates and salts thereof, alkyl methyl taurates (e.g., C12-C30), and soaps (e.g., alkali metal salts, e.g., sodium or potassium salts) of fatty acids.

Amphoteric and zwitterionic surfactants are also useful herein. Examples of amphoteric and zwitterionic surfactants which can be used in the compositions of the present invention are those which are broadly described as derivatives of aliphatic secondary and tertiary amines in which the aliphatic radical can be straight or branched chain and wherein one of the aliphatic substituents contains from about 8 to about 22 carbon atoms (preferably C8-C18) and one contains an anionic water solubilizing group, e.g., carboxy, sulfonate, sulfate, phosphate, or phosphonate. Examples are alkyl imino acetates, and iminodialkanoates and aminoalkanoates, imidazolinium and ammonium derivatives. Other suitable amphoteric and zwitterionic surfactants are those selected from the group consisting of betaines, sultaines, hydroxysultaines, alkyl sarcosinates (e.g., C12-C30), and alkanoyl sarcosinates.

The liquid core compositions of the present invention may include a silicone containing emulsifier or surfactant. A wide variety of silicone emulsifiers are useful herein. These silicone emulsifiers are typically organically modified organopolysiloxanes, also known to those skilled in the art as silicone surfactants. Useful silicone emulsifiers include dimethicone copolyols. These materials are polydimethyl siloxanes which have been modified to include polyether side chains such as polyethylene oxide chains, polypropylene oxide chains, mixtures of these chains, and polyether chains containing moieties derived from both ethylene oxide and propylene oxide. Other examples include alkyl-modified dimethicone copolyols, i.e., compounds which contain C2-C30 pendant side chains. Still other useful dimethicone copyols include materials having various cationic, anionic, amphoteric, and zwitterionic pendant moieties.

Dimethicone copolyol emulsifiers may be also be used. Nonlimiting examples of dimethicone copolyols and other silicone surfactants useful as emulsifiers herein include polydimethylsiloxane polyether copolymers with pendant polyethylene oxide sidechains, polydimethylsiloxane polyether copolymers with pendant polypropylene oxide sidechains, polydimethylsiloxane polyether copolymers with pendant mixed polyethylene oxide and polypropylene oxide sidechains, polydimethylsiloxane polyether copolymers with pendant mixed poly(ethylene)(propylene)oxide sidechains, polydimethylsiloxane polyether copolymers with pendant organobetaine sidechains, polydimethylsiloxane polyether copolymers with pendant carboxylate sidechains, polydimethylsiloxane polyether copolymers with pendant quaternary ammonium sidechains; and also further modifications of the preceding copolymers containing pendant C2-C30 straight, branched, or cyclic alkyl moieties. Examples of commercially available dimethicone copolyols useful herein sold by Dow Corning Corporation are DOW CORNING 190, 193, Q2-5220, 2501 Wax, 2-5324 fluid, and 3225C (the later material being sold as a mixture with cyclomethicone). Cetyl dimethicone copolyol is commercially available as a mixture with polyglyceryl-4 isostearate (and) hexyl laurate and is sold under the tradename ABIL® WE-09 (available from Goldschmidt). Cetyl dimethicone copolyol is also commercially available as a mixture with hexyl laurate (and) polyglyceryl-3 oleate (and) cetyl dimethicone and is sold under the tradename ABIL® WS-08 (also available from Goldschmidt). Other nonlimiting examples of dimethicone copolyols also include lauryl dimethicone copolyol, dimethicone copolyol acetate, dimethicone copolyol adipate, dimethicone copolyolamine, dimethicone copolyol behenate, dimethicone copolyol butyl ether, dimethicone copolyol hydroxy stearate, dimethicone copolyol isostearate, dimethicone copolyol laurate, dimethicone copolyol methyl ether, dimethicone copolyol phosphate, and dimethicone copolyol stearate.

The Shell

The shell comprises hydrophobic particles. As used herein, "hydrophobic" includes both hydrophobic particles per se and hydrophobized particles obtained by reaction of the surface of hydrophilic particles with a hydrophobic surface modifying agent.

Useful hydrophobic particles include, but are not limited to, silicone- or silane-coated powders, or fluoropolymer-coated powders, such as talc, kaolin, mica, sericite, dolomite, phlogopite, synthetic mica, lepidolite, biotite, lithia mica, vermiculite, magnesium carbonate, calcium carbonate, aluminum silicate, barium silicate, calcium silicate, magnesium silicate, strontium silicate, tungstenic acid metal salts, magnesium, silica, zeolite, barium sulfate, calcined calcium sulfate, calcium phosphate, fluorapatite, hydroxyapatite, titania, fumed titania, zinc oxide, alumina and fumed alumina. Other hydrophobic particles include, but are not limited to, particles of hydrophobic compounds or polymers, such as solid long chain fatty acids and their esters, alcohols, and metal salts (e.g., stearic acid, stearyl alcohol, and magnesium stearate), hydrophobic waxes (e.g., paraffin wax and beeswax), and fluoropolymers (e.g., polyvinylfluoride, polyvinylidene fluoride, polytetrafluoroethylene, polychlorotrifluoroethylene, perfluoroalkoxy polymer, fluorinated ethylene-propylene, polyethylenetetrafluoroethylene, polyethylenechlorotrifluoroethylene, perfluorinated elastomer, fluorocarbon, chlorotrifluoroethylenevinylidene fluoride and, perfluoropolyether.

Among these, hydrophobized silica particles that form a three dimensional network, an aggregated structure, are a preferred shell material. The silica may be a precipitated silica or a fumed silica, the latter being preferred. Fumed silica is obtained in a flame hydrolysis or flame oxidation process. Its purity is higher than 99 wt %, usually higher than 99.8 wt %. Fumed silica usually forms a three-dimensional network of aggregated primary particles and is porous. The fumed silica primary particles bear hydroxyl groups at their surface and are nonporous.

Other hydrophobic fumed metal oxides may also be used, such as hydrophobic fumed titanium oxide and aluminum oxide, such as Aeroxide. $TiO_2$ T805, and Aeroxide Alu C805 (both from EVONIK, Piscataway, N.J.).

Precipitated and fumed silica particles, as well as other hydrophilic particles may be hydrophobized in a subsequent step. Procedures for this step are known to the person skilled in the art.

WO2011/076518 discloses these and other hydrophobic or hydrophobized silica particles suitable for use as the shell material of the present invention.

Hydrophobic surface modifying agents include silanes, including .organosilanes, holoorganosilanes, and cyclinc polysiloxanes, which may be used individually or as a mixture. Examples of hydrophobic surface modifying agents include octyltrimethoxysilane, octyltriethoxysilane, hexamethyldisilazane, hexadecyltrimethoxysilane, hexadecyltriethoxysilane, dimethylpolysiloxane, nonafluorohexyltrimethoxysilane, tridecafluorooctyltrimethoxysilane, and tridecafluorooctyltriethoxysilane. With particular preference, it is possible to use hexamethyldisilazane, octyltriethoxysilane and dimethyl polysiloxanes.

The hydrophobic particles may be hydrophobized silica particles having a BET surface area of 30 $m^2/g$ to 500 $m^2/g$, or 100 $m^2/g$ to 350 $m^2/g$. Due to the reaction with the surface modifying agent these particles may contain 0.1 to 15 wt %, usually 0.5 to 5 wt %, of carbon.

Examples of useful hydrophobic particles include AEROSIL® R104 (octamethylcyclotetrasiloxane; 150 m2/g; 55); AEROSIL® R106 (octamethylcyclotetrasiloxane; 250 m2/g; 50), AEROSIL® R202 (polydimethylsiloxane; 100 $m_2/g$; 75), AEROSIL ® R805 (octylsilane; 150 m2/g; 60), AEROSIL® R812 (hexamethyldisilazane; 260 $m^2/g$; 60), AEROSIL® R812S (hexamethyldisilazane; 220 $m^2/g$; 65), and AEROSIL® R8200 (hexamethyldisilazane; 150 $m^2/g$; 65). The indications in parenthesis refer to the surface modifying agent, the approximate BET surface area and the approximate methanol wettability.

It may also be beneficial to use hydrophobized fumed silica particles in compacted form or as granules.

Other suitable hydrophobic particles include fine inorganic, organic, or polymeric fine powders coated with silicone, silane or fluoro-compounds, which can be used alone or as mixture with hydrophobic silica or hydrophobic fumed silica powder.

The amount of hydrophobic particles in the powder is about 2% to about 30%, or about 2.5% to about 20%, or about 3% to about 10%, or about 3% to about 8%, by weight based on the total weight of powder (comprising core/shell particles).

In one embodiment, the shell consists of hydrophobized fumed silica particles that are obtained by reacting a hydrophilic fumed silica having a BET surface area of from 30 to 500 $m^2/g$.

In another embodiment, the hydrophobized fumed silica particles are obtained by reacting a hydrophilic fumed silica having a BET surface area from 270 to 330 $m^2/g$ with hexamethyldisilazane to give hydrophobized fumed silica particles having a BET surface area of from 200 to 290 m$^2$/g and a carbon content of 2 to 4 wt % and methanol wettability of at least 50.

In one embodiment, active agents and/or additional ingredients are present in the shell.

Second Powder

The powder comprising core/shell particles is mixed with a second powder of a color cosmetic. The color cosmetic may be a foundation, a rouge, a concealer, an eye shadow and the like. Alternatively, inorganic and/or organic pigments that are used in any of the color cosmetics may be added to the first powder and blended to make compositions of the present invention. The amount of color cosmetic or organic or inorganic pigment may range from about 0.001% to about 90%, for example from about 1% to about 50% by weight or from about 0.01 to about 90% by weight or from about 5% to about 25% by weight based on the total weight of the composition. The mixing process is usually done during the product manufacturing process, namely, the second powder is mixed with the powder of core/shell particles (i.e., the first powder) as a powder mixture after the latter have been manufactured. However, the mixing process may also be carried out post-manufacturing by a user prior to use. In this case, the second powder and powder comprising core/shell particles may be packaged in a dual chamber container or separate containers.

In one embodiment, the second powder comprises one or more solid active agents, liquid actives impregnated into absorbent powder materials, solid cosmetic/pharmaceutical formulation excipients, or liquid cosmetic/pharmaceutical formulation excipients impregnated into absorbent powder materials.

Solid active agents in a powder form that may be used in the second powder include unstable actives such as certain vitamins (e.g., ascorbic acid), and natural extracts containing antioxidants suitable for use in the compositions of this invention, include, but not limited to plant extracts containing flavonoids, phenolic compounds including procyanidins of different sizes (e.g., dimers, trimers and oligomers), and proanthocyanidins, flavones, flavanones, isoflavonoids, mono-, di- and tri-terpenes, sterols and their derivatives. Examples of such plant extracts include grape seed, green tea, pine bark and propolis extracts, cotinus coggygria, barley and legume extracts and the like.

Absorbent powder materials include pharmaceutically or cosmetically acceptable porous powders such as silica and fumed silica, powders of starches, and clays, synthetic and natural fibers, as well as the materials described as useful for the hydrophobic particles of the shell.

Method of Making Core/Shell Particles

A single phase liquid core can be made by simple blending or mixing of the liquid ingredients until uniform. High shearing is not required for this step, as blending of miscible liquids does not require high energy. The liquid mixing for this step may be done with equipment such as blenders, lab scale mixers, or homogenizers. The sample may be heated in cases where an active agent contained therein requires higher temperature to dissolve in the liquid mixture. The resulting homogeneous liquid can be converted to a powder by mixing with the hydrophobic particles of the shell under high shear, such as with a blender or a rotor-stator mixer or other inline high rotational speed mixers. It is preferred to run the powderization step with all contents at room temperature or below.

In the case of a liquid core comprising an emulsion, the ingredients of the liquid core, including immiscible liquids, and/or active agents, and emulsifiers are mixed together under high shear until an emulsion is formed. The mixing for this step may be done with equipment such as blenders or homogenizers. The sample may be heated in cases where the active agent requires a higher temperature to dissolve in the liquid. The resulting emulsion can be converted to a powder by mixing with the hydrophobic particles under high shear, such as with a blender or a rotor-stator mixer or other inline high rotational speed mixers. It is preferred to run the powderization step with all contents at room temperature or below.

Methods of using high rotational speed mixers for powder-liquid mixing to prepare the core/shell compositions are known in the art. The energy of mixing should be high enough to break the liquid into fine droplets to be covered or encapsulated by the hydrophobic powder shell. L. Forny et. al. ("Influence of mixing characteristics for water encapsulation by self-assembling hydrophobic silica nanoparticles," Powder Technology 189, 2009, pages 263-269) describe the method and requirements for such preparation, which is incorporated herein by reference in its entirety.

Use

The powder comprising core/shell particles has great versatility in application, and can be used in many consumer and medical products for human and animal use such as topical compositions (such as creams, lotions, gels, shampoos, cleansers, powder patches, and masks for application to the skin).

The powder comprising core/shell particles may contain a wide range of active agents used for various applications as described in the sections below.

The powder comprising core/shell particles may be administered topically to a subject (e.g., a human) in need of treatment for a condition or disease, or to otherwise provide a therapeutic effect. Such therapeutic effects include, but are not limited to: anti-inflammation effects including effects in the superficial or deep tissues (e.g., reduce or elimination of soft tissue redness); or improving body appearance (e.g., effects on body contour or shape).

The powder comprising core/shell particles may be combined with one or more other active agents not contained in a second powder.

Topical Skin Compositions

In one embodiment, the invention provides a topical composition containing the powder comprising core/shell particles that is suitable for administering to mammalian skin, such as human skin. In one embodiment, such topical composition contains a safe and effective amount of (i) the powder comprising core/shell particles, and (ii) a cosmetically- or pharmaceutically-acceptable carrier.

The topical compositions may be made into a wide variety of products that include but are not limited to leave-on products (such as lotions, creams, gels, sticks, sprays, and ointments), film-forming products (such as masks), make-up (such as foundations, eye liners, and eye shadows), and the like. These product types may contain any of several cosmetically- or pharmaceutically-acceptable carrier forms including, but not limited to solutions, suspensions, emulsions such as microemulsions and nanoemulsions, gels, and solids carrier forms. Other product forms can be formulated by those of ordinary skill in the art.

In one embodiment, the topical composition is used for the treatment of skin conditions. Examples of such skin conditions include, but are not limited to acne (e.g., blackheads and whiteheads), rosacea, nodule-cystic, and other microbial infections of the skin; visible signs of skin aging (e.g., wrinkles, sagging, sallowness, and age-spots); loose or lax skin, folliculitis and pseudo-folliculitis barbae; excess sebum (e.g., for sebum reduction or oily/shining skin appearance inhibition or control); pigmentation (e.g., for reduction of hyperpigmentation such as freckles, melasma, actinic and senile lentigines, age-spots, post-inflammatory hypermelanosis, Becker's naevus, and facial melanosis or enhancing the pigmentation of light skin); excess hair growth (e.g., skin on the leg), or insufficient hair growth (e.g., on the scalp); dermatitis (e.g., atopic, contact, or seborrheic dermatitis), dark circles under the eye, stretch marks, cellulite, excessive sweating (e.g., hyperhidrosis), and/or psoriasis.

(a) Topical Anti-Acne/Anti-Rosacea Compositions

In one embodiment, the topical composition also contains an anti-acne and/or anti-rosacea active agent. Examples of anti-acne and anti-rosacea agents include, but are not limited to: retinoids such as tretinoin, isotretinoin, motretinide, adapalene, tazarotene, azelaic acid, and retinol; salicylic acid; resorcinol; sulfacetamide; urea; antibiotics such as tetracycline, clindamycin, metronidazole, and erythromycin; anti-inflammatory agents such as corticosteroids (e.g., hydrocortisone), ibuprofen, naproxen, and hetprofen; and imidazoles such as ketoconazole and elubiol; and salts and prodrugs thereof. Other examples of anti-acne active agents include essential oils, alpha-bisabolol, dipotassium glycyrrhizinate, camphor, β-glucan, allantoin, feverfew, flavonoids such as soy isoflavones, saw palmetto, chelating agents such as EDTA, lipase inhibitors such as silver and copper ions, hydrolyzed vegetable proteins, inorganic ions of chloride, iodide, fluoride, and their nonionic derivatives chlorine, iodine, fluorine, and synthetic phospholipids and natural phospholipids such as ARLASILKTM phospholipids CDM, SV, EFA, PLN, and GLA (commercially available from Uniqema, ICI Group of Companies, Wilton, UK).

(b) Topical Anti-Aging Compositions

In one embodiment, the topical composition also contains an anti-aging agent. Examples of suitable anti-aging agents include, but are not limited to; retinoids; dimethylaminoethanol (DMAE), copper containing peptides, vitamins such as vitamin E, vitamin A (retinol and its derivatives, e.g., retinyl palmitate), vitamin C (ascorbic acid and its derivative, e.g., Ascorbic Acid 2-Glucoside/AA2G), and vitamin B (e.g., niacinamide, niacin) and vitamin salts or derivatives such as ascorbic acid di-glucoside and vitamin E acetate or palmitate; alpha hydroxy acids and their precursors such as glycolic acid, citric acid, lactic acid, malic acid, mandelic acid, ascorbic acid, alpha-hydroxybutyric acid, alpha-hydroxyisobutyric acid, alpha-hydroxyisocaproic acid, atrrolactic acid, alpha-hydroxyisovaleric acid, ethyl pyruvate, galacturonic acid, glucoheptonic acid, glucoheptono 1,4-lactone, gluconic acid, gluconolactone, glucuronic acid, glucuronolactone, isopropyl pyruvate, methyl pyruvate, mucic acid, pyruvic acid, saccharic acid, saccharic acid 1,4-lactone, tartaric acid, and tartronic acid; beta hydroxy acids such as beta-hydroxybutyric acid, beta-phenyl-lactic acid, and beta-phenylpyruvic acid; tetrahydroxypropyl ethylene-diamine, N,N,N',N'-Tetrakis(2-hydroxypropyl)ethylenediamine (THPED); and botanical extracts such as green tea, soy, milk thistle, algae, aloe, angelica, bitter orange, coffee, goldthread, grapefruit, hoellen, honeysuckle, Job's tears, lithospermum, mulberry, peony, puerarua, nice, and safflower; and salts and prodrugs thereof.

(c) Topical Depigmentation Compositions

In one embodiment, the topical composition contains a depigmentation agent. Examples of suitable depigmentation agents include, but are not limited to: soy extract; soy isoflavones; retinoids such as retinol; kojic acid; kojic dipalmitate; hydroquinone; arbutin; transexamic acid; vitamins such as niacinamide, niacin and vitamin C (ascorbic acid and AA2G; azelaic acid; linolenic acid and linoleic acid; placertia; licorice; and extracts such as chamomile, grape seeds and green tea; and salts and prodrugs thereof.

(d) Topical Antipsoriatic Compositions

In one embodiment, the topical composition contains an antipsoriatic active agent. Examples of antipsoriatic active agents (e.g., for seborrheic dermatitis treatment) include, but are not limited to, corticosteroids (e.g., betamethasone dipropionate, betamethasone valerate, clobetasol propionate, diflorasone diacetate, halobetasol propionate, triamcinonide, dexamethasone, fluocinonide, fluocinolone acetonide, halcinonide, triamcinolone acetate, hydrocortisone, hydrocortisone verlerate, hydrocortisone butyrate, aclometasone dipropionte, flurandrenolide, mometasone furoate, methylprednisolone acetate), methotrexate, cyclosporine, calcipotriene, anthraline, shale oil and derivatives thereof, elubiol, ketoconazole, coal tar, salicylic acid, zinc pyrithione, selenium sulfide, hydrocortisone, sulfur, menthol, and pramoxine hydrochloride, and salts and prodrugs thereof.

(e) Other Topical Ingredients

In one embodiment, the topical composition contains a plant extract as an active agent. Examples of plant extracts include, but are not limited to, feverfew, soy, glycine soja, oatmeal, what, aloe vera, cranberry, witch-hazel, alnus, arnica, artemisia capillaris, asiasarum root, birch, calendula, chamomile, cnidium, comfrey, fennel, galla rhois, hawthorn, houttuynia, hypericum, jujube, kiwi, licorice, magnolia, olive, peppermint, philodendron, salvia, sasa albo-marginata, natural isoflavonoids, soy isoflavones, and natural essential oils.

In one embodiment, the topical composition contains one or more buffering agents such as citrate buffer, phosphate buffer, lactate buffer, gluconate buffer, or gelling agent, thickener, or polymer.

In one embodiment, the composition or product contains a fragrance effective for reducing stress, calming, and/or affecting sleep such as lavender and chamomile.

The powder comprising core/shell particles can be incorporated into compositions for the treatment of periodontal disease with actives such as, but not limited to minocycline.

EXAMPLES

Examples are set forth below to further illustrate the nature of the invention and the manner of carrying it out. However, the invention should not be considered as being limited to the details thereof.

Example 1

A core/shell particulate formulation was prepared as follows:

TABLE 1

| Ingredient of the Liquid Core | Weight Percentage |
| --- | --- |
| Silicone fluid Q7-9120, 20 cst, Dow Corning | 40 |
| Glycerol, anhydrous | 57.3 |
| STRUCTURE ®PS-111 | 2.7 |
| Wt %: | 100 |

STRUCTURE ®PS-111 is sodium hydrolyzed potato starch dodecenylsuccinate (Akzo Nobel).

The liquids in Table 1 were blended to make a core composition. The core material was made into a core/shell particulate with 92% (w/w) the liquid core and 8% (w/w) hydrophobic fumed silica powder (R812S, EVONIK Industries) by adding the above liquid mixture into a high speed blender (e.g.Oster Blender model BCBG08) with fumed silica at room temperature and the mixture was blended at the highest setting for about 10-20 seconds, yielding an off-white powder. This core/shell particulate contained 36.8% silicone fluid Q7-9120 (skin conditioning agent) and 52.7% glycerol (moisturizing agent).

A commercial cosmetic foundation powder product, Neutrogena® Mineral Sheer Loose Powder Foundation, Nude 40 (NTG MS Powder) was mixed with the powder-to-cream particulate formulation of Table 1. NTG MS Powder contains Titanium Dioxide (7.5%) as active ingredient (sunscreen), and following inactive ingredients: Active Ingredients: Titanium Dioxide 7.5%. Inactive Ingredients: Mica, Polymethyl Methacrylate, Zinc Stearate, Silk Powder, Sodium Dehydroacetate, Methylparaben, Propylparaben, Glycine Soja (Soybean) Flour, Tocopheryl Acetate, Pantothenic Acid, Retinyl Palmitate, Ascorbic Acid. May Contain: Bismuth Oxychloride, Iron Oxides, Titanium Dioxide.

Two powder mixtures were prepared by mixing the powder-to-cream of Table 1 with NTG MS Powder to yield uniform powder mixtures: Powder Mixture A containing weight 50% powder-to-cream particulates, and Powder Mixture B containing 0.01%. The Powder Mixture A contains 18.4% silicone fluid Q7-9120 and 26.4% glycerol, both which are well known to provide skin moisturizing benefits, especially the latter. Tests were performed with the Powder Mixture A for oil absorption capability.

An in vitro test was performed to demonstrate the superior oil absorption of the powder Mixture A, as compared to the commercial NTG MS Powder. Briefly, the test followed the following steps: (1) 80 grams of distilled water was placed into each of the two weighing boats (Large VWR Hexagonal Polystyrene Weighing Boats, 5½ Inch wide); (2) four drops of a plant oil (BioChemica Sweet Almond Oil, The HallStar Company, Chicago, Ill. 60606) were add to the water in each weighing boat to form a visible thin oil layer on the water surface; (3) 0.05 g of the powder Mixture A was placed onto the oil layer in one weighing boat, and the same amount of NTG MS Powder was placed onto the oil layer in the other weighing boat. It was observed that Powder Mixture A spread out immediately and covered most of the water surface, and the presence of the oil layer could be seen significantly reduced. In contrast, the NTG MS Powder did not spread at all, and did not show any effect on the oil layer. Since almond oil contains saturated and unsaturated fatty acids and esters, resembling somewhat the sebum and oil substances on human skin, this test result indicates that the mixture of the core/shell mixture with a commercial cosmetic foundation powder would have the cosmetic benefit of oil/shine control on the skin, while providing skin moisturization due to the presence of glycerol and silicone fluid, both well-known skin moisturizing ingredients.

While the invention has been described above with reference to specific embodiments thereof, it is apparent that many changes, modifications, and variations can be made without departing from the inventive concept disclosed herein. Accordingly, it is intended to embrace all such changes, modifications, and variations that fall within the spirit and broad scope of the appended claims.

We claim:

1. A composition comprising powder comprising a first powder of core/shell particles having an average particle size of less than 1000 microns, each particle comprising:
    a liquid core that is free of water that comprises a polar liquid having a percent surface polarity of at least 24%, wherein said liquid core comprises glycerol, silicone oil and sodium hydrolyzed potato starch dodecenylsuccinate and is an oil glycerol emulsion, and
    a shell comprising hydrophobic particles; and
    a second powder comprising a color cosmetic.

2. The powder of claim 1, wherein the hydrophobic particles comprise hydrophobic fumed silica.

3. A method for enhancing the topical application of a color cosmetic which comprises topically administering to a human or animal the powder composition according to claim 1.

4. The powder of claim 1, wherein the cosmetic is selected from the group consisting of eye shadow, foundation, blush and concealer.

5. The powder of claim 1, wherein the amount of color cosmetic is from about 0.001% to about 90% by weight based on the total weight of the composition.

6. The powder of claim 5, wherein the amount of color cosmetic is from about 0.01% to about 90% by weight based on the total weight of the composition.

7. The powder of claim 6, wherein the amount of color cosmetic is from about 1% to about 50% by weight based on the total weight of the composition.

8. The powder of claim 7, wherein the amount of color cosmetic is from about 5% to about 25% by weight based on the total weight of the composition.

* * * * *